(12) United States Patent
Chen et al.

(10) Patent No.: US 7,425,572 B2
(45) Date of Patent: Sep. 16, 2008

(54) USE OF DIOXINDOINDAZOLES AND DIOXOLOINDAZOLES FOR TREATING GLAUCOMA

(75) Inventors: Hwang-Hsing Chen, Fort Worth, TX (US); Jesse A. May, Fort Worth, TX (US)

(73) Assignee: Alcon, Inc., Hunenberg (CH)

( * ) Notice: Subject to any disclaimer, the term of this patent is extended or adjusted under 35 U.S.C. 154(b) by 537 days.

(21) Appl. No.: 11/293,018

(22) Filed: Dec. 2, 2005

(65) Prior Publication Data

US 2006/0122251 A1 Jun. 8, 2006

Related U.S. Application Data

(60) Provisional application No. 60/634,170, filed on Dec. 8, 2004.

(51) Int. Cl.
*A61K 31/416* (2006.01)
*C07D 231/54* (2006.01)

(52) U.S. Cl. .......... 514/405; 548/356.1; 548/358.1; 548/359.1; 548/359.5; 514/403; 544/106; 544/111; 544/140; 544/358; 546/184

(58) Field of Classification Search .......... 548/356.1, 548/358.1, 359.1, 359.5; 514/403, 405; 544/106, 111, 140, 358; 546/184
See application file for complete search history.

(56) References Cited

U.S. PATENT DOCUMENTS

| | | | |
|---|---|---|---|
| 4,690,931 A | 9/1987 | Wick et al. | 514/317 |
| 5,011,846 A | 4/1991 | Gittos et al. | 514/294 |
| 5,151,444 A | 9/1992 | Ueno et al. | 514/530 |
| 5,290,781 A | 3/1994 | Espino et al. | 514/259 |
| 5,296,504 A | 3/1994 | Stjernschantz et al. | 514/530 |
| 5,352,708 A | 10/1994 | Woodward et al. | 514/729 |
| 5,422,368 A | 6/1995 | Stjernschantz et al. | 514/530 |
| 5,494,928 A | 2/1996 | Bös | 514/415 |
| 5,538,974 A | 7/1996 | Ogawa et al. | 514/253 |
| 5,561,150 A | 10/1996 | Wichmann | 514/406 |
| 5,571,833 A | 11/1996 | Kruse et al. | 514/414 |
| 5,578,612 A | 11/1996 | Macor et al. | 514/323 |
| 5,646,173 A | 7/1997 | Bös et al. | 514/411 |
| 5,652,272 A | 7/1997 | Ogawa et al. | 514/652 |
| 5,874,477 A | 2/1999 | McConnell et al. | 514/657 |
| 5,889,052 A | 3/1999 | Klimko et al. | 514/530 |
| 5,902,815 A | 5/1999 | Olney et al. | 514/285 |
| 6,107,324 A | 8/2000 | Behan et al. | 514/406 |
| 6,353,002 B2 | 3/2002 | Birch et al. | 514/321 |
| 6,660,870 B1 | 12/2003 | Ruskinko et al. | 548/307.4 |
| 6,664,286 B1 | 12/2003 | May et al. | 514/415 |
| 6,696,476 B2 * | 2/2004 | Chen et al. | 514/403 |
| 6,806,285 B1 | 10/2004 | May et al. | 514/416 |
| 6,881,749 B2 * | 4/2005 | Chen et al. | 514/403 |
| 6,884,816 B2 | 4/2005 | May et al. | 514/405 |
| 6,933,392 B2 | 8/2005 | May et al. | 548/359.1 |

FOREIGN PATENT DOCUMENTS

| | | |
|---|---|---|
| EP | 0 771 563 B1 | 1/2003 |
| WO | WO 92/20338 | 11/1992 |
| WO | WO 94/03162 | 2/1994 |
| WO | WO 94/13275 | 6/1994 |
| WO | WO 94/24121 | 10/1994 |
| WO | WO 97/35579 | 10/1997 |
| WO | WO 98/18458 | 5/1998 |
| WO | WO 98/31354 | 7/1998 |
| WO | WO 98/40386 | 9/1998 |
| WO | WO 99/59499 | 11/1999 |
| WO | WO 00/12475 | 3/2000 |
| WO | WO 00/12510 | 3/2000 |
| WO | WO 00/35922 | 6/2000 |
| WO | WO 00/44753 | 8/2000 |
| WO | WO 00/77002 | 12/2000 |
| WO | WO 00/77010 | 12/2000 |
| WO | WO 01/12602 | 2/2001 |
| WO | WO 01/40183 | 6/2001 |
| WO | WO 01/70207 | 9/2001 |
| WO | WO 01/70223 | 9/2001 |
| WO | WO 01/70230 | 9/2001 |
| WO | WO 01/70701 | 9/2001 |
| WO | WO 01/70702 | 9/2001 |
| WO | WO 01/70745 | 9/2001 |
| WO | WO 02/088133 | 11/2002 |
| WO | WO 02/098350 | 12/2002 |
| WO | WO 02/098400 | 12/2002 |
| WO | WO 02/098860 | 12/2002 |
| WO | WO 03/051291 | 6/2003 |
| WO | WO 03/051352 | 6/2003 |

(Continued)

OTHER PUBLICATIONS

Chang et al., "Mechanism of the Ocular Hypotensive Action of Ketanserin," *J. of Ocular Pharmacology*, vol. 1(2), pp. 137-147 (1985).

Fiorella et al., "Role of 5-$HT_{2A}$ and 5-$HT_{2C}$ receptors in the stimulus effects of hallucinogenic drugs II: reassessment of LSD false positives," *Psychopharmacology*, vol. 121, pp. 357-363 (1995).

Gupta et al., "Therapeutic Potentials of 5-HT Receptor Modulators," *Indian J. of Pharmacology*, vol. 26, pp. 94-107 (1994).

(Continued)

*Primary Examiner*—Golam M Shameem
(74) *Attorney, Agent, or Firm*—Patrick M. Ryan

(57) ABSTRACT

Novel dioxinoindazole compounds and dioxoloindazole compounds are disclosed. Also disclosed are methods for the lowering and controlling of normal or elevated intraocular pressure as well as a method for the treatment of glaucoma using compositions of one or more of the compounds of the present invention.

10 Claims, No Drawings

FOREIGN PATENT DOCUMENTS

| WO | WO 03/053436 | 7/2003 |
| WO | WO 03/101379 | 12/2003 |
| WO | WO 2004 019874 | 3/2004 |
| WO | WO 2004/028451 | 4/2004 |
| WO | WO 2004/054572 | 7/2004 |
| WO | WO 2004/058725 | 7/2004 |

OTHER PUBLICATIONS

Krootila et al., "Effect of Serotonin and Its Antagonist (Ketanserin) on Intraocular Pressure in the Rabbit," *J. of Ocular Pharmacology*, vol. 3(4), pp. 279-290 (1987).

Mallorga et al., "Characterization of Serotonin Receptors in the Iris + ciliary body of the albino rabbit," *Current Eye Research*, vol. 6(3), pp. 527-532 (1987).

Mano et al., "The Effect of Anplag (Sarpogelate HCL), New Selective 5-$HT_2$ Antagonist on Intraocular Pressure in Rabbits," *IOVS*, vol. 36(4), S719 (1995).

May et al., "A Novel and Selective 5-$HT_2$ Receptor Agonist with Ocular Hypotensive Activity: (S)-(+)-1-(2-Aminopropyl)-8,9-dihydropyrano[3,2-e]indole," *J. Med. Chem.*, vol. 46, pp. 4188-4195 (2003).

May et al., "Evaluation of the Ocular Hypotensive Response of Serotonin 5-$HT_{1A}$ and 5-$HT_2$ Receptor Ligands in Conscious Ocular Hypertensive Cynomolgus Monkeys," *J. of Pharmacology and Experimental Therapeutics*, vol. 306(1), pp. 301-309 (2003).

Michne et al., "Novel Inhiitors of the Nuclear Factor of Activated T Cells (NFAT)-Mediated Transcription of β-Galactosidase: Potential Immunosupressive and Antiinflammatory Agents," *J. Med. Chem*, vol. 38, pp. 2557-2569 (1995).

Osborne et al., "Do Beta-Adrenoceptors and Serotonin 5-$HT_1$A Receptors have Similar Functions in the control of Intraocular Pressure in the Rabbit?", *Ophthalmologica*, vol. 210, pp. 308-314 (1996).

Osborne et al., "5-Hydroxytryptamine$_{1A}$ agonists: potential use in glaucoma. Evidence from animal studies," *Eye*, vol. 14(38), pp. 454-463 (2000).

Takeda et al., "The Effect of Inplag. Novel Selective 5-$HT_2$ Antagonist on Intraocular Pressure in Glaucoma Patients," *IOVS*, Vo. 36(4), S734 (1995).

Vellaccio et al., "Catechol and Substituted Catechol-Derived Ortho Esters, Models for Protected Active Esters in Peptide Synthesis," *J. Org. Chem.*, vol. 46, pp. 3087-3091 (1981).

Wang et al., "Effect of 5-methylurapidil, an $\alpha_{1a}$-adrenergic antagonist and 5-hydroxytryptamine$_{1a}$ agonist, on aqueous humor dynamics in monkeys and rabbits," *Current Eye Research*, vol. 16(8), pp. 769-775 (1997).

Wang et al., "Effect of $_p$MPPI Hydrochloride (p-MPPI) Applied before 5-methylurapidil (5-MU) on Intraocular Pressure (IOP) in Normal Monkeys," *IOVS*, vol. 39(4) (1998).

\* cited by examiner

USE OF DIOXINDOINDAZOLES AND DIOXOLOINDAZOLES FOR TREATING GLAUCOMA

This application claims priority to U.S. Provisional Application, U.S. Ser. No. 60/634,170 filed Dec. 8, 2004.

BACKGROUND OF THE INVENTION

1. Field of the Invention

The present invention relates to various dioxinoindazoles. These novel compounds are useful for lowering and controlling normal or elevated intraocular pressure (IOP) and for treating glaucoma.

2. Description of the Related Art

The disease state referred to as glaucoma is characterized by a permanent loss of visual function due to irreversible damage to the optic nerve. The several morphologically or functionally distinct types of glaucoma are typically characterized by elevated IOP, which is considered to be causally related to the pathological course of the disease. Ocular hypertension is a condition wherein intraocular pressure is elevated but no apparent loss of visual function has occurred; such patients are considered to be at high risk for the eventual development of the visual loss associated with glaucoma.

If glaucoma or ocular hypertension is detected early and treated promptly with medications that effectively reduce elevated intraocular pressure, loss of visual function or its progressive deterioration can generally be ameliorated. Drug therapies that have proven to be effective for the reduction of intraocular pressure include both agents that decrease aqueous humor production and agents that increase the outflow facility. Such therapies are in general administered by one of two possible routes, topically (direct application to the eye) or orally.

There are some individuals who do not respond well when treated with certain existing glaucoma therapies. There is, therefore, a need for other topical therapeutic agents that control IOP.

Serotonergic 5-$HT_{1A}$ agonists have been reported as being neuroprotective in animal models and many of these agents have been evaluated for the treatment of acute stroke among other indications. This class of compounds has been mentioned for the treatment of glaucoma (lowering and controlling IOP), see e.g., WO 98/18458 (DeSantis, et al.) and EP0771563A2 (Mano, et al.). Osborne, et al. (Ophthalmologica, Vol. 210:308-314, 1996) teach that 8-hydroxydipropylaminotetralin (8-OH-DPAT) (a 5-$HT_{1A}$ agonist) reduces IOP in rabbits. Wang, et al. (Current Eye Research, Vol. 16(8):769-775, August 1997, and IOVS, Vol. 39(4), S488, March, 1998) indicate that 5-methylurapidil, an $\alpha_{1A}$ antagonist and 5-$HT_{1A}$ agonist lowers IOP in the monkey, but due to its $\alpha_{1A}$ receptor activity. Also, 5-$HT_{1A}$ antagonists are disclosed as being useful for the treatment of glaucoma (elevated IOP) (e.g., WO 92/0338, McLees). Furthermore, DeSai, et al. (WO 97/35579) and Macor, et al. (U.S. Pat. No. 5,578,612) relate to the use of 5-$HT_1$ and 5-$HT_{1-like}$ agonists for the treatment of glaucoma (elevated IOP). These anti-migraine compounds, e.g., sumatriptan and naratriptan and related compounds, are 5-$HT_{1B,D,E,F}$ agonists.

It has been found that serotonergic compounds which possess agonist activity at 5-$HT_2$ receptors effectively lower and control normal and elevated IOP and are useful for treating glaucoma, see U.S. Pat. No. 6,664,286, incorporated in its entirety by reference herein. Compounds that act as agonists at 5-$HT_2$ receptors are well known and have shown a variety of utilities, primarily for disorders or conditions associated with the central nervous system (CNS). U.S. Pat. No. 5,494,928 relates to certain 2-(indol-1-yl)-ethylamine derivatives that are 5-$HT_{2C}$ agonists for the treatment of obsessive compulsive disorder and other CNS derived personality disorders U.S. Pat. No. 5,571,833 relates to tryptamine derivatives that are 5-$HT_2$ agonists for the treatment of portal hypertension and migraine. U.S. Pat. No. 5,874,477 relates to a method for treating malaria using 5-$HT_{2A/2C}$ agonists. U.S. Pat. No. 5,902,815 relates to the use of 5-$HT_{2A}$ agonists to prevent adverse effects of NMDA receptor hypo-function. WO98/31354 relates to 5-$HT_{2B}$ agonists for the treatment of depression and other CNS conditions. WO 00/12475 relates to indoline derivatives and WO 00/12510 and WO00/44753 relate to certain indole derivatives as 5-$HT_{2B}$ and 5-$HT_{2C}$ receptor agonists for the treatment of a variety of disorders of the central nervous system, but especially for the treatment of obesity. WO 00/35922 relates to certain pyrazino[1,2-a]quinoxaline derivates as 5-$HT_{2C}$ agonists for the treatment of obsessive compulsive disorder, depression, eating disorders, and other disorders involving the CNS. WO 00/77002 and WO 00/77010 relate to certain substituted tetracyclic pyrido [4,3-b]indoles as 5-$HT_{2C}$ agonists with utility for the treatment of central nervous system disorders including obesity, anxiety, depression, sleep disorders, cephalic pain, and social phobias among others. Agonist response at the 5-$HT_{2A}$ receptor is reported to be the primary activity responsible for hallucinogenic activity, with some lesser involvement of the 5-$HT_{2C}$ receptor possible [Psychopharmacology, Vol. 121:357, 1995].

Few dioxino-indazoles or dioxolo-indazoles have been reported. Certain unexemplified [1,4]dioxino[2,3-g]indazole compounds are within the broadly defined definition for compounds of U.S. Pat. No. 6,353,002 which are reported to have utility in the treatment of certain central nervous system disorders. However, the compounds of the present application are unlike those of the U.S. Pat. No. 6,353,002. A few dioxinoindoles and dioxoloindoles have been reported. International Patent, WO200101260, reports the synthesis and use of condensed indoline derivatives as 5-HT, in particular 5-$HT_{2C}$, receptor ligands for the treatment of disorders of the central nervous system; cardiovascular disorders; gastrointestinal disorders; diabetes insipidus, and sleep apnea, and particularly the treatment of obesity. The application includes the synthesis of (S)-1-(2,3,7,8-tetrahydro-9H-1,4-dioxino-[2,3-g]indol-9-yl)-2-propylamine flimarate and other analogs.

Accordingly, there is a need to provide new compounds, which avoid the disadvantages, described above and which provide increased chemical stability and a desired length of therapeutic activity, for instance, in decreasing intraocular pressure and treating glaucoma.

SUMMARY OF THE PRESENT INVENTION

The present invention overcomes these and other drawbacks of the prior art by providing novel compounds which are 5-$HT_2$ agonists.

The present invention further provides compounds which have increased chemical stability and which are useful in lowering and controlling normal or elevated intraocular pressure and/or treating glaucoma.

Another feature of the present invention is to provide compounds, which provide a desired level of therapeutic activity in lowering and controlling normal or elevated intraocular pressure and/or treating glaucoma.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates to a compound having the Formula I: or pharmaceutically acceptable salts or solvates or prodrug forms of the compounds of Formula I.

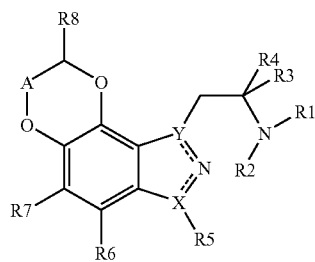

(I)

In the formula, $R^1$ and $R^2$ are independently chosen from hydrogen or $C_{1-4}$ alkyl;

$R^3$ and $R^4$ are independently chosen from hydrogen or $C_{1-4}$ alkyl or;

$R^3$ and $R^4$ and the carbon atom to which they are attached can form a cycloalkyl ring, or furthermore, $R^2$ and $R^3$ together can be $(CH_2)_m$ to form a saturated heterocycle;

$R^5$ is chosen from hydrogen, halogen, $C_{1-6}$ alkyl or $C_{1-4}$ alkyl substituted by halogen;

$R^6$ and $R^7$ are independently chosen from hydrogen, halogen, cyano, $C_{1-4}$ alkylthio, $C_{1-4}$ alkyl, or $C_{1-4}$ alkyl substituted by halogen;

$R^8$ and $R^9$ are independently chosen from hydrogen, $C_{1-6}$ alkyl, $C_{1-6}$alkoxy, $=O$, $NR^{10}R^{11}$, $OC(=O)NR^1R^2$, $OC(=O)C_{1-4}$alkyl, $C_{1-6}$ alkylthiol, $C_{1-6}$ alkyl substituted with halogen, or $NR^{10}R^{11}$, $OR^{12}$, $CO_2R^{13}$, $CONR^{14}R^{15}$, $SO_2R^{12}$, $NSO_2R^{12}$, $SO_2NR^{10}R^{11}$;

$R^{10}$ and $R^{11}$ are independently chosen from hydrogen, $C_{1-4}$ alkyl, $C(=O)C_{1-4}$ alkyl, $C(=O)OC_{1-4}$ alkyl, $C(=O)NR^1R^2$, or $C_{1-4}$ alkyl substituted with halogen, hydroxyl, $NR^1R^2$ or $R^{10}$ and $R^{11}$ together can complete a saturated 5 or 6-membered heterocyclic ring, which can include an additional heteroatom selected from N, O, or S when a 6-membered ring;

$R^{12}$ is hydrogen, $C_{1-6}$ alkyl, $C(=O)C_{1-6}$alkyl, $C(=O)OC_{1-6}$ alkyl, $C(=O)N(R^{13})C_{1-6}$alkyl or $C(=O)C_{1-6}$alkyl substituted by hydroxyl, $C_{1-4}$alkoxide, or halide;

$R^{13}$ is hydrogen, $C_{1-6}$alkyl, $C_{1-6}$alkyl substituted by hydroxyl, $C_{1-4}$alkoxy, or halide;

$R^{14}$ and $R^{15}$ are independently chosen from hydrogen, hydroxyl, $C_{1-4}$alkoxy, $C_{1-6}$alkyl, $C_{2-6}$alkyl substituted by hydroxyl, $C_{1-4}$alkoxy, halide, or $R^{14}$ and $R^{15}$ can be combined to form a saturated heterocyclic ring selected from pyrrolidine, piperidine, piperazine, or morpholine;

m=2-4;

A=$CHR^9$ or no atom;

X and Y are either N or C, wherein X and Y are different from each other; and the dashed bonds denotes a suitably appointed single and double bond.

DETAILED DESCRIPTION OF THE PREFERRED EMBODIMENTS

The present invention relates to a compound having the Formula I, or pharmaceutically acceptable salts or solvates or prodrug forms of the compounds of Formula I.

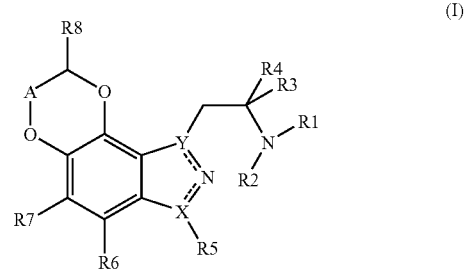

(I)

In the formula, $R^1$ and $R^2$ are independently chosen from hydrogen or $C_{1-4}$ alkyl;

$R^3$ and $R^4$ are independently chosen from hydrogen or $C_{1-4}$ alkyl or;

$R^3$ and $R^4$ and the carbon atom to which they are attached can form a cycloalkyl ring, or furthermore, $R^2$ and $R^3$ together can be $(CH_2)_m$ to form a saturated heterocycle;

$R^5$ is chosen from hydrogen, halogen, $C_{1-6}$ alkyl or $C_{1-4}$ alkyl substituted by halogen;

$R^6$ and $R^7$ are independently chosen from hydrogen, halogen, cyano, $C_{1-4}$ alkylthio, $C_{1-4}$ alkyl, or $C_{1-4}$ alkyl substituted by halogen;

$R^8$ and $R^9$ are independently chosen from hydrogen, $C_{1-6}$ alkyl, $C_{1-6}$alkoxy, $=O$, $NR^{10}R^{11}$, $OC(=O)NR^1R^2$, $OC(=O)C_{1-4}$alkyl, $C_{1-6}$ alkylthiol, $C_{1-6}$ alkyl substituted with halogen, or $NR^{10}R^{11}$, $OR^{12}$, $CO_2R^{13}$, $CONR^{14}R^{15}$, $SO_2R^{12}$, $NSO_2R^{12}$, $SO_2NR^{10}R^{11}$;

$R^{10}$ and $R^{11}$ are independently chosen from hydrogen, $C_{1-4}$ alkyl, $C(=O)C_{1-4}$ alkyl, $C(=O)OC_{1-4}$ alkyl, $C(=O)NR^1R^2$, or $C_{1-4}$ alkyl substituted with halogen, hydroxyl, $NR^1R^2$ or $R^{10}$ and $R^{11}$ together can complete a saturated 5 or 6-membered heterocyclic ring, which can include an additional heteroatom selected from N, O, or S when a 6-membered ring;

$R^{12}$ is hydrogen, $C_{1-6}$ alkyl, $C(=O)C_{1-6}$alkyl, $C(=O)OC_{1-6}$ alkyl, $C(=O)N(R^{13})C_{1-6}$alkyl or $C(=O)C_{1-6}$alkyl substituted by hydroxyl, $C_{1-4}$alkoxide, or halide;

$R^{13}$ is hydrogen, $C_{1-6}$alkyl, $C_{1-6}$alkyl substituted by hydroxyl, $C_{1-4}$alkoxy, or halide;

$R^{14}$ and $R^{15}$ are independently chosen from hydrogen, hydroxyl, $C_{1-4}$alkoxy, $C_{1-6}$alkyl, $C_{2-6}$alkyl substituted by hydroxyl, $C_{1-4}$alkoxy, halide, or $R^{14}$ and $R^{15}$ can be combined to form a saturated heterocyclic ring selected from pyrrolidine, piperidine, piperazine, or morpholine;

m=2-4;

A=$CHR^9$ or no atom;

X and Y are either N or C, wherein X and Y are different from each other; and the dashed bonds denotes a suitably appointed single and double bond.

Preferred Compounds are those of Formula I wherein:

$R^1$ and $R^2$ are independently chosen from hydrogen or $C_{1-4}$ alkyl;

$R^3$ and $R^4$ are independently chosen from hydrogen or $C_{1-4}$ alkyl or $R^2$ and $R^3$ together can be $(CH_2)_m$ to form a saturated heterocycle;

$R^5$ is chosen from hydrogen, halogen, or $C_{1-6}$ alkyl;

$R^6$ and $R^7$ are independently chosen from hydrogen, halogen, cyano, $C_{1-4}$ alkylthio, $C_{1-4}$ alkyl, or $C_{1-4}$ alkyl substituted by halogen;

$R^8$ and $R^9$ are independently chosen from hydrogen, $C_{1-6}$ alkyl, $C_{1-6}$alkoxy, =O, $NR^{10}R^{11}$, $OC(=O)NR^1R^2$, $OC(=O)C_{1-4}$alkyl, a $C_{1-6}$ alkyl substituted with halogen, or $NR^{10}R^{11}$, $OR^{11}$, $CO_2R^{11}$, $CON R^{10}R^{11}$, $SO_2R^{11}$, $NSO_2R^{11}$, $SO_2NR^{10}R^{11}$;

$R^{10}$ and $R^{11}$ are independently chosen from hydrogen, $C_{1-4}$ alkyl, $C(=O)C_{1-4}$ alkyl, $C(=O)OC_{1-4}$ alkyl, $C(=O)NR^1R^2$, or $C_{1-4}$ alkyl substituted with halogen, hydroxyl, $NR^1R^2$ or $R^{10}$ and $R^{11}$ together can complete a saturated 5 or 6-membered heterocyclic ring, which can include an additional heteroatom selected from N, O, or S;

m=2-4;

A=$CHR^9$ or no atom;

X and Y are either N or C, wherein X and Y are different from each other; and the dashed bonds denotes a suitably appointed single and double bond.

Most Preferred Compounds of Formula I are those wherein:

$R^1$ and $R^2$ are independently chosen from hydrogen or $C_{1-4}$ alkyl;

$R^3$ is $C_{1-2}$ alkyl or $R^2$ and $R^3$ together can be $(CH_2)_3$ to form a pyrrolidine;

$R^4$ is hydrogen;

$R^5$ is chosen from hydrogen, halogen, or $C_{1-4}$ alkyl;

$R^6$ and $R^7$ are independently chosen from hydrogen, halogen, $C_{1-4}$ alkyl;

$R^8$ and $R^9$ are independently chosen from hydrogen, $C_{1-4}$ alkyl, a $C_{1-4}$ alkyl substituted with halogen, or $NR^{10}R^{11}$, $OR^{11}$, $CO_2R^{11}$, $CONR^{11}R^{11}$, $SO_2R^{11}$, $NSO_2R^{11}$;

$R^{10}$ and $R^{11}$ are independently chosen from hydrogen, $C_{1-4}$ alkyl, $C(=O)C_{1-4}$ alkyl, $C(=O)OC_{1-4}$ alkyl, $C(=O)NR^1R^2$, or $C_{1-4}$ alkyl substituted with halogen, hydroxyl, $NR^1R^2$ or $R^{10}$ and $R^{11}$ together can complete a saturated 5 or 6-membered heterocyclic ring, which can include an additional heteroatom selected from N, O, or S;

A=$CHR^9$ or no atom;

X and Y are either N or C, wherein X and Y are different from each other; and the dashed bonds denotes a suitably appointed single and double bond.

Representative Examples of Preferred Compounds of Formula I are:

2-(7,8-Dihydro-[1,4]dioxino[2,3-g]indazol-1-yl)-1-methylethylamine;

(S)-2-(7,8-Dihydro-[1,4]dioxino[2,3-g]indazol-1-yl)-1-methyl-ethylamine;

(R)-2-(7,8-Dihydro-[1,4]dioxino[2,3-g]indazol-1-yl)-1-methyl-ethylamine;

[1-(2-Amino-propyl)-7,8-dihydro-1H-[1,4]dioxino[2,3-g]indazol-8-yl]-methanol;

[1-((S)-2-Amino-propyl)-7,8-dihydro-1H-[1,4]dioxino[2,3-g]indazol-8-yl]-methanol;

[(R)-1-((S)-2-Amino-propyl)-7,8-dihydro-1H-[1,4]dioxino[2,3-g]indazol-8-yl]-methanol;

[(S)-1-((S)-2-Amino-propyl)-7,8-dihydro-1H-[1,4]dioxino[2,3-g]indazol-8-yl]-methanol;

N-[1-((S)-2-Amino-propyl)-7,8-dihydro-1H-[1,4]dioxino[2,3-g]indazol-8-ylmethyl]-methanesulfonamide;

N-[(S)-1-((S)-2-Amino-propyl)-7,8-dihydro-1H-[1,4]dioxino[2,3-g]indazol-8-ylmethyl]-methanesulfonamide;

Ethanesulfonic acid [1-((S)-2-amino-propyl)-7,8-dihydro-1H-[1,4]dioxino[2,3-g]indazol-8-ylmethyl]-amide;

Ethanesulfonic acid [(S)-1-((S)-2-amino-propyl)-7,8-dihydro-1H-[1,4]dioxino[2,3-g]indazol-8-ylmethyl]-amide;

[1-((S)-2-Amino-propyl)-7,8-dihydro-1H-[1,4]dioxino[2,3-g]indazol-8-ylmethyl]-carbamic acid methyl ester;

[(S)-1-((S)-2-Amino-propyl)-7,8-dihydro-1H-[1,4]dioxino[2,3-g]indazol-8-ylmethyl]-carbamic acid methyl ester;

2-((S)-8-Aminomethyl-7,8-dihydro-[1,4]dioxino[2,3-g]indazol-1-yl)-1-methyl-ethylamine;

(S)-2-((S)-8-Aminomethyl-7,8-dihydro-[1,4]dioxino[2,3-g]indazol-1-yl)-1-methyl-ethylamine;

N-({1-[(S)-2-aminopropyl]-7,8-dihydro-1H-[1,4]dioxino[2,3-g]indazol-8-yl}methyl)acetamide;

N-({(S)-1-[(S)-2-aminopropyl]-7,8-dihydro-1H-[1,4]dioxino[2,3-g]indazol-8-yl}methyl)acetamide;

1-(1H-[1,3]dioxolo[4,5-g]indazol-1-yl))-1-methyl-ethylamine;

(S)-1-(1H-[1,3]dioxolo[4,5-g]indazol-1-yl))-1-methyl-ethylamine;

or combinations thereof.

Certain compounds of Formula I can contain one or more chiral centers. The present invention contemplates all enantiomers, diastereomers, and mixtures thereof.

In the above definitions, the total number of carbon atoms in a substituent group is indicated by the $C_{i-j}$ prefix where the numbers i and j define the number of carbon atoms. This definition includes straight chain, branched chain, and cyclic alkyl or (cyclic alkyl)alkyl groups. A substituent may be present either singly or multiply when incorporated into the indicated structural unit. For example, the substituent halogen, which means fluorine, chlorine, bromine, or iodine, would indicate that the unit to which it is attached may be substituted with one or more halogen atoms, which may be the same or different.

SYNTHESIS

The compounds of Formula I can be prepared by using one of several synthetic procedures. For example [1-(2-Amino-propyl)-7,8-dihydro-1H-[1,4]dioxino[2,3-g]indazol-1yl]-methanols can be prepared from an appropriately protected 1-(6-hydroxylindazole-1-yl)-propan-2-ol as outlined in Scheme 1. Pg denotes a suitable protective group to assure that a particular atom is not modified during the indicated chemical reaction.

Other compounds of Formula I can be prepared from 12 through selected functional group transformations well known in the art. For example, initial protection of the primary amine group followed by activation of the hydroxyl group by the formation of a sulfonate ester, e.g. methanesulfonyl, and subsequent reaction with a desired nucleophile such as alkylamines, dialkylamines, aryl or alkylthiols, and the alike, and after the deprotection of the amine group will provide compounds 15 of formula I. Furthermore, oxidation of 14 with suitable oxidizing agent provides the acid 17, which can be converted to the ester and amide 16 as shown in Scheme 2.

Scheme 2
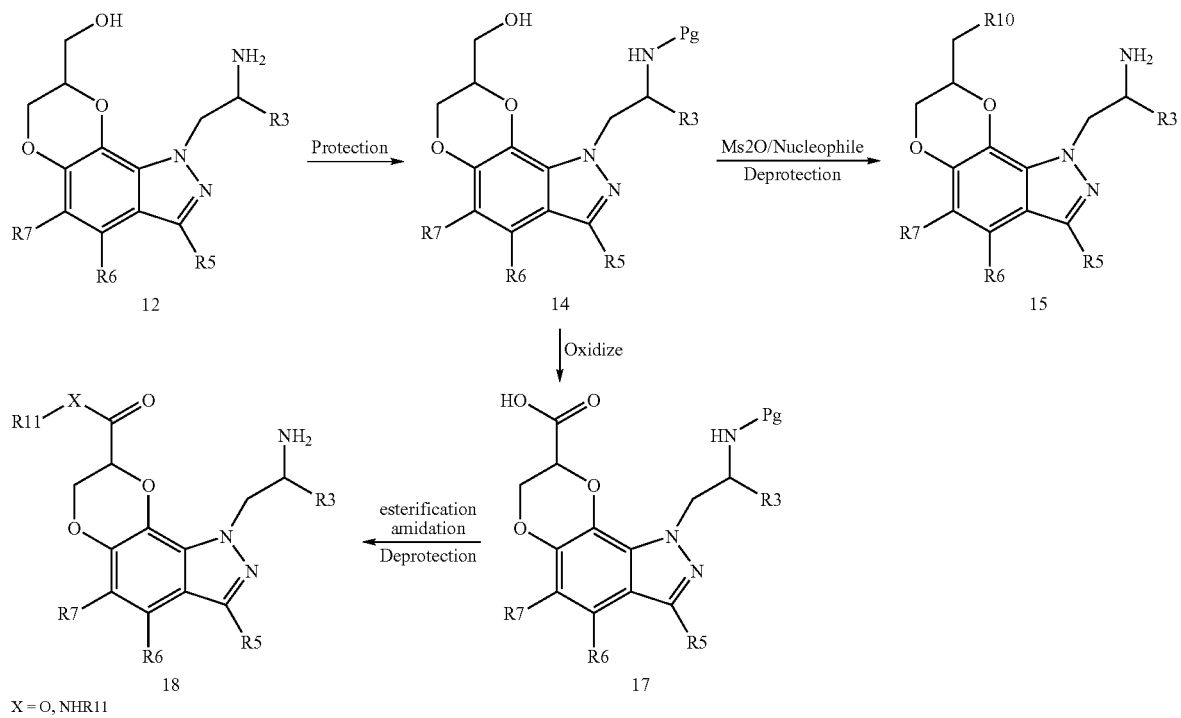
Alternately, compounds of Formula I can be prepared from appropriately substituted compound 3 via intramolecular cyclization [J. Am. Chem. Soc., Vol. 123, No. 49, 12202-12206 (2001)] to give the intermediate 7,8-dihydro-1H-[1,4]dioxo[2,3-g]indazoles which can be converted to the compounds of Formula I as shown in the Scheme 3.
Scheme 3
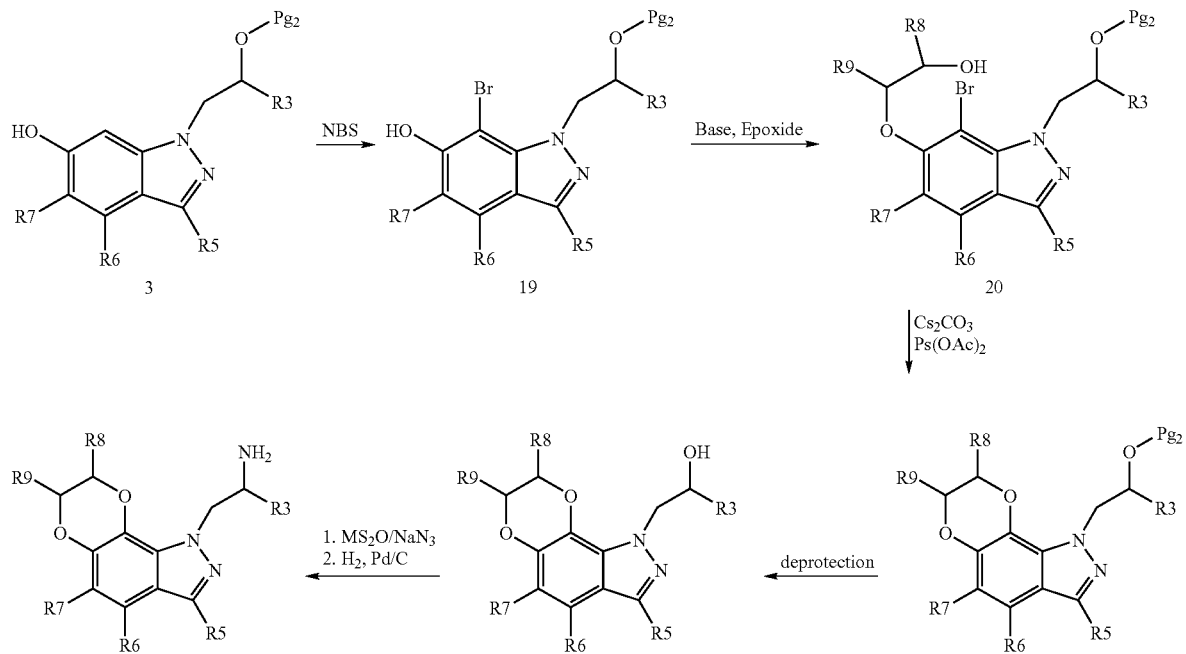

Compounds of Formula I (A=no atom) can be prepared from starting material 24. Diazotization of 24 and reduction with zinc gives an intermediate hydrazine-aldehyde that reacts and affords the indazole 25. Alkylation of 25 with propylene oxide gives the corresponding alcohol 26 that can be converted to 27 and then 28 using the same procedures as shown in the Scheme 1.

Alternately, compounds of Formula I (A=no atom) can be prepared from the intermediate 5. Protection the phenol 5 with benzyl group and oxidation with MCPBA give the diphenol (catechol) 32 after deprotection. The catechol can be converted to the corresponding benzo[1,3]dioxole 33 according to known procedures (J. Org. Chem., 46, 15, p 3087-3091, 1981 and J. Med. Chem., 38, 14, p 2557-2569, 1995). The

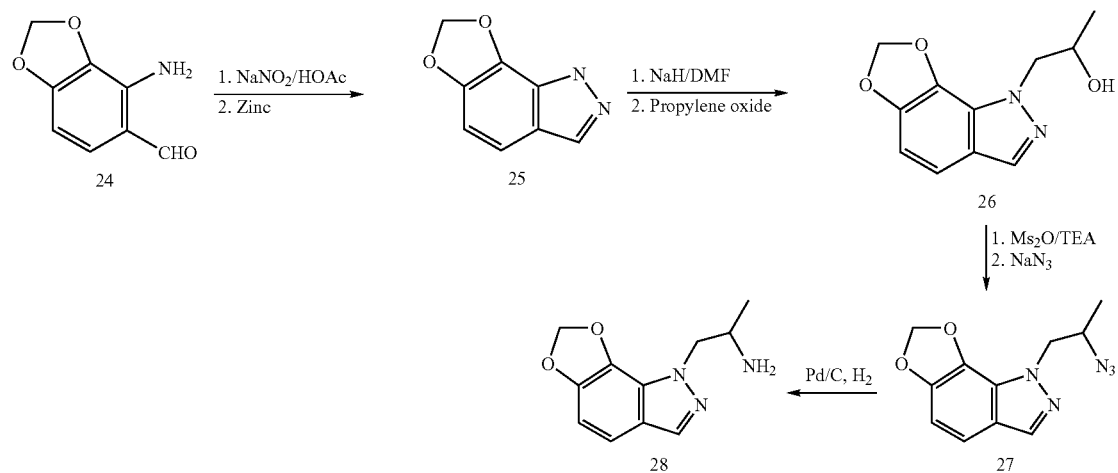

dioxole 33 can be converted to the compounds of the Formula I using similar procedures as shown in Scheme 1.

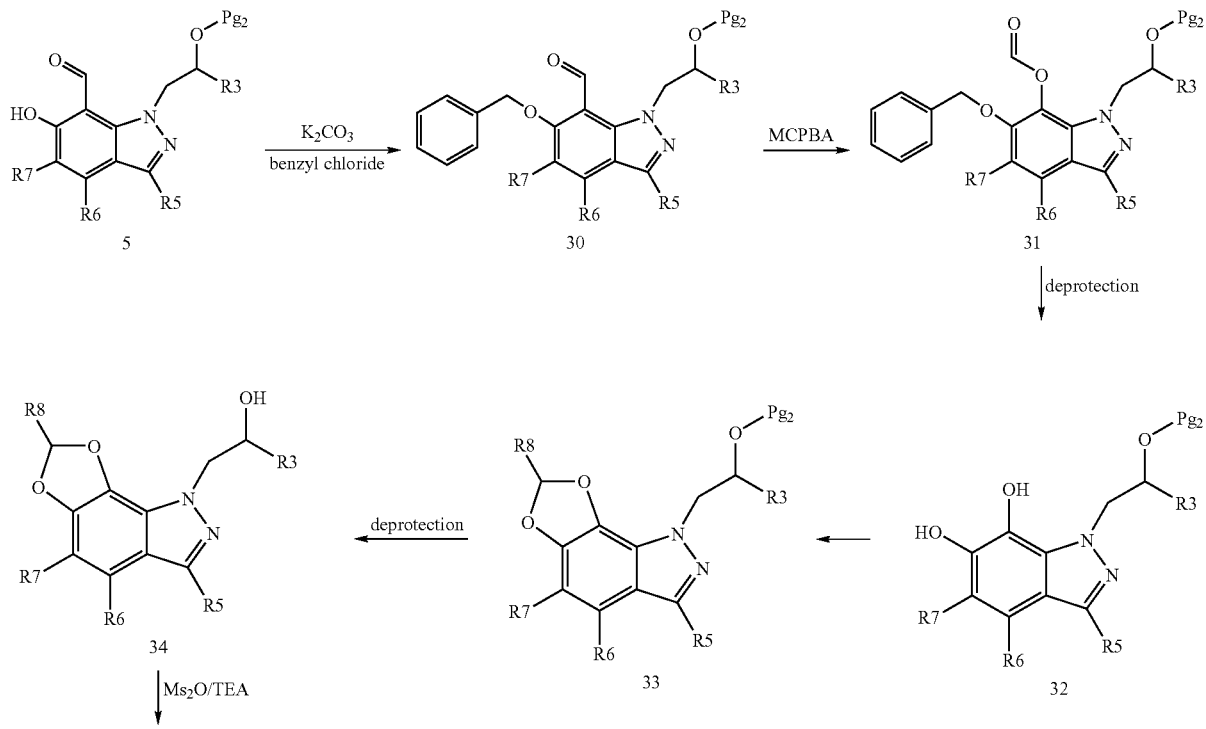

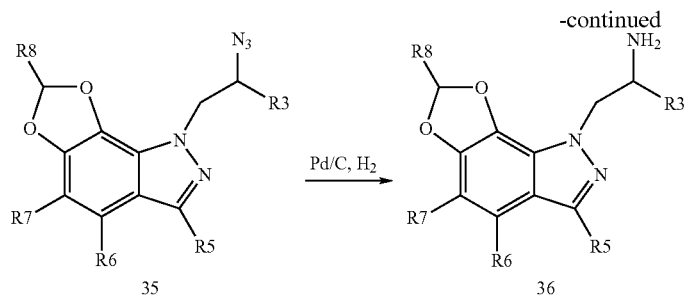

Using the procedures described in the scheme 1-5 (above), the example 1-4 (below), and well known procedures, one skilled in the art can prepared the compounds disclosed herein. Preferred compounds according to the present invention are those set forth in Table 1-2, below. In Table 1-3, the following abbreviations correspond to the indicated structural elements: Me is methyl; Et is ethyl; Pr is propyl; iBu is isobutyl; Ac is acetyl.

TABLE 1

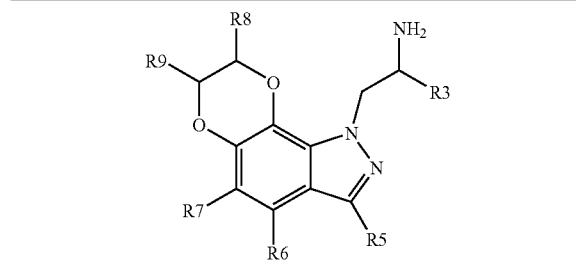

| $R^3$ | $R^5$ | $R^6$ | $R^7$ | $R^8$ | $R^9$ |
|---|---|---|---|---|---|
| Me | H | H | H | $(CH_2)_3OH$ | H |
| Me | H | H | H | $(CH_2)_2OH$ | H |
| Me | H | H | H | $CH_2OH$ | H |
| Me | H | H | H | $(CH_2)_2NH_2$ | H |
| Me | H | H | H | $(CH_2)_2NH(C=O)CH_3$ | H |
| Me | H | H | H | $(CH_2)_2NH(C=O)OCH_3$ | H |
| Me | H | H | H | $(CH_2)_2NH(C=O)NCH_3$ | H |
| Me | H | H | H | $(CH_2)_2NH(C=O)Et$ | H |
| Me | H | H | H | $(CH_2)_2NH(C=O)Pr$ | H |
| Me | H | H | H | $(CH_2)_2NH(C=O)Bu$ | H |
| Me | H | H | H | $(CH_2)_2NH(C=O)iPr$ | H |
| Me | H | H | H | $(CH_2)_2NH(C=O)iBu$ | H |
| Me | H | H | H | $(CH_2)_2NH(C=O)OEt$ | H |
| Me | H | H | H | $(CH_2)_2NH(C=O)OPr$ | H |
| Me | H | H | H | $(CH_2)_2NH(C=O)OBu$ | H |
| Me | H | H | H | $(CH_2)_2NH(C=O)OiPr$ | H |
| Me | H | H | H | $(CH_2)_2NH(C=O)OiBu$ | H |
| Me | H | H | H | $(CH_2)_2NH(C=O)NEt$ | H |
| Me | H | H | H | H | $(CH_2)_3OH$ |
| Me | H | H | H | H | $(CH_2)_2OH$ |
| Me | H | H | H | H | $CH_2OH$ |
| Me | H | H | H | H | $(CH_2)_2NH_2$ |
| Me | H | H | H | H | $(CH_2)_2NH(C=O)CH_3$ |
| Me | H | H | H | H | $(CH_2)_2NH(C=O)OCH_3$ |
| Me | H | H | H | H | $(CH_2)_2NH(C=O)NCH_3$ |
| Me | H | H | H | $CH_2SMe$ | H |
| Me | H | H | H | $CH_2S(=O)Me$ | H |
| Me | H | H | H | $CH_2S(=O)_2Me$ | H |
| Me | H | H | H | $C(=O)OMe$ | H |
| Me | H | H | H | $C(=O)NHMe$ | H |
| Me | H | H | H | $C(=O)NMe_2$ | H |
| Me | H | H | H | $CH_2CN$ | H |
| Me | H | H | H | $CH_2O(CH)_2OH$ | H |

TABLE 2

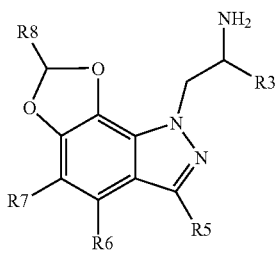

| $R^3$ | $R^5$ | $R^6$ | $R^7$ | $R^8$ |
|---|---|---|---|---|
| Me | H | H | H | $(CH_2)_3OH$ |
| Me | H | H | H | $(CH_2)_2OH$ |
| Me | H | H | H | $CH_2OH$ |
| Me | H | H | H | $(CH_2)_2NH_2$ |
| Me | H | H | H | $(CH_2)_2NH(C=O)CH_3$ |
| Me | H | H | H | $(CH_2)_2NH(C=O)OCH_3$ |
| Me | H | H | H | $(CH_2)_2NH(C=O)NCH_3$ |
| Me | H | H | H | $(CH_2)_2NH(C=O)Et$ |
| Me | H | H | H | $(CH_2)_2NH(C=O)Pr$ |
| Me | H | H | H | $(CH_2)_2NH(C=O)Bu$ |
| Me | H | H | H | $(CH_2)_2NH(C=O)iPr$ |
| Me | H | H | H | $(CH_2)_2NH(C=O)iBu$ |
| Me | H | H | H | $(CH_2)_2NH(C=O)OEt$ |
| Me | H | H | H | $(CH_2)_2NH(C=O)OPr$ |
| Me | H | H | H | $(CH_2)_2NH(C=O)OBu$ |
| Me | H | H | H | $(CH_2)_2NH(C=O)OiPr$ |
| Me | H | H | H | $(CH_2)_2NH(C=O)OiBu$ |
| Me | H | H | H | $(CH_2)_2NH(C=O)NEt$ |
| Me | H | H | H | $CH_2SMe$ |
| Me | H | H | H | $CH_2S(=O)Me$ |
| Me | H | H | H | $CH_2S(=O)_2Me$ |
| Me | H | H | H | $C(=O)OMe$ |
| Me | H | H | H | $C(=O)NHMe$ |
| Me | H | H | H | $C(=O)NMe_2$ |
| Me | H | H | H | $CH_2CN$ |
| Me | H | H | H | $CH_2O(CH)_2OH$ |

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Preparation 1 (Synthesis of a Synthetic Intermediate)

Benzyl [(1S)-2-(7-formyl-6-hydroxy-1H-indazol-1-yl)-1-methylethyl]carbamate

Step A: Benzyl {(1S)-2-[6-hydroxy-7-(hydroxymethyl)-1H-indazol-1-yl]-1-methylethyl}carbamate.

A solution of benzyl [(1S)-2-(6-hydroxy-1H-indazol-1-yl)-1-methylethyl]carbamate (30.83 g, 0.0949 mol) in THF (400 ml) was treated with aqueous concentrated formaldehyde (37%, 12 M. 0.285 mol, 24 mL) and cooled in an ice bath. To the mixture was slowly added aqueous 1 N sodium hydroxide (0.02 mol, 20 mL) and the reaction was allowed to warm to room temperature while stirring overnight. The reaction was quenched with aqueous saturated sodium bicarbonate (250 mL) and then neutralized to pH 7 with aqueous 2 N hydrochloric acid. The mixture was extracted with ethyl acetate (200 mL×3), the combined organic layers were dried over magnesium sulfate and filtered and evaporated to give crude tan solid, 28.38 g, which was a mixture of desired product and dimerized byproduct by LC/MS 356 m/z and 663 m/z. This residue was purified by chromatography (silica gel, hexane/ethyl acetate 1:1) to give the title compound, (18.44 g, 56%) as a yellow foamy solid, which was not pure by LS/MS 354 m/z with minor 663 m/z.

Step B: Benzyl [(1S)-2-(7-formyl-6-hydroxy-1H-indazol-1-yl)-1-methylethyl]carbamate A solution of the compound from Step A (18.44 g, 0.0519 mol) in ethyl acetate (180 mL) was treated with mangenese dioxide (fine powder, 18 g) and stirred at 45-50° C. for two days. Then the reaction stood at room temperature one day. The mixture was filtered and the black solids were rinsed with ethyl acetate. The organic filtrate was evaporated to a tan foam. The residue was purified by chromatography (silica gel, hexane/ethyl acetate 1:1) to give the title compound, (6.32 g, 35%) as a pale yellow fluffy solid, which was pure by LS/MS 354 m/z.

EXAMPLE 1

[(S)-1-((S)-2-Amino-propyl)-7,8-dihydro-1H-[1,4]dioxino[2,3-g]indazol-8-yl]-methanol hydrochloride

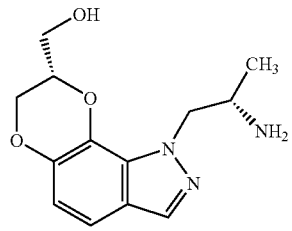

(Example 1)

Step A: {(S)-2-[7-Formyl-6-((R)-1-oxiranylmethoxy)-indazol-1-yl]-1-methyl-ethyl}-carbamic acid benzyl ester To a stirred solution of the phenol from Preparation 1 (2.00 g, 5.67 mmol) in anhydrous N,N-dimethylformamide (DMF, 50 mL) was added NaH (60% dispersion in mineral oil, 0.227 g, 5.67 mmol) under nitrogen atmosphere. After 10 min (2R)-(-)-glycidyl tosylate (1.94 g, 8.51 mmol) was added and the mixture was heated at 70° C. for 1 h. Potassium carbonate (0.39 g, 2.84 mmol) was added and heating was continued for additional 1.5 h. DMF was evaporated and the residue was mixed with a saturated aqueous solution of sodium bicarbonate (50 mL) then extracted with ethyl acetate (50 mL×3). The combined extracts were dried over magnesium sulfate, filtered and evaporated to dryness. Chromatography on silica eluting with a gradient of 20% to 60% ethyl acetate/hexane gave the desired product as an oil (1.92 g, 83%) and starting material (0.27 g, 13%). LCMS (+APCI) m/z 410 (M+H), $^1$H NMR (600 MHz, CDCl$_3$) δ 10.67 (s, 1H), 7.95 (s, 1H), 7.89 (d, J=12 Hz, 1H), 7.32-7.26 (m, 5H), 7.22 (d, J=6 Hz, 1H), 6.87 (d, J=6 Hz, 1H), 5.49 (d, J=6 Hz, 1H), 4.97-4.87 (m, 2H), 4.85-4.82 (m, 2H), 4.43 (dd, J=12, 6 Hz, 1H), 4.16 (bd, 2H), 3.41 (s, 1H), 2.96 (1H), 2.78 (m, 1H), 1.19 (d, J=12 Hz, 3H).

Step B: [(S)-2-((S)-8-Hydroxymethyl-7,8-dihydro-[1,4]dioxino[2,3-g]indazol-1-yl)-1-methyl-ethyl]-carbamic acid benzyl ester To a 0° C. stirred solution of the epoxide from Step A (0.71 g, 1.73 mmol) in dichloromethane (50 mL) was added m-chloroperbenzoic acid (70%, 0.514 g, 2.08 mmol) under nitrogen atmosphere. After the addition was completed the reaction mixture was allowed to warm to ambient temperature and stirred for 5 h. The reaction was quenched by a saturated aqueous solution of sodium thiosulfate (10 mL) and dichloromethane was evaporated. To the aqueous residue was added potassium carbonate (1.00 g) and methanol (100 mL), the resulting mixture was stirred for 1 h and methanol was evaporated. The residue was extracted with ethyl acetate (50 mL×3), dried and evaporated to dryness to afford an oil. Chromatography on silica eluting with a gradient of 0% to 10% acetone/dichloromethane gave a solid (0.24 g, 35%). mp 116-117° C., LCMS (+APCI) m/z 397 (M+H), $^1$H NMR (600 MHz, CDCl$_3$) δ 7.82 (s, 1H), 7.36-7.29 (m, 5H), 7.14 (d, J=9.0 Hz, 1H), 6.75 (d, J=8.4 Hz, 1H), 5.08-5.02 (m, 4H), 4.34-4.16 (m, 4H), 4.01 (d, J=12.6 Hz, 1H), 3.83 (m, 1H), 1.07 (d, J=6.6 Hz, 3H).

Step C: [(S)-1-((S)-2-Aminopropyl)-7,8-dihydro-1H-[1,4]dioxino[2,3-g]indazol-8-yl]-methanol hydrochloride A solution of the alcohol from Step B (0.14 g, 0.35 mmol) and palladium on carbon (10%, 0.016 g) in methanol (50 mL) was stirred under hydrogen atmosphere overnight. The progress of reaction was monitored by TLC. The catalyst was removed by filtration and the filtrate was treated a 2N HCl/EtOH (about 2 mL). Evaporation gave a white hygroscopic foamy solid (0.096 g, 91%). mp 202-203° C., LCMS (+APCI) m/z 264 (M+H), $^1$H NMR (600 MHz, CD$_3$OD) δ 7.85 (s, 1H), 7.11 (d, J=9.0, 1H), 6.69 (d, J=9.0 Hz, 1H), 4.69 (dd, J=4.8, 6.6 Hz, 2H), 4.31 (dd, J=2.4, 11.4 Hz, 1H), 4.29 (m, 1H), 4.07 (dd, J=6.6, 11.4 Hz, 1H), 3.81 (dd, J=4.2, 12.6 Hz, 1H), 3.74 (m, 2H), 1.21 (d, J=6.6 Hz, 3H). Anal. for (C$_{10}$H$_{13}$N$_3$O+HCl+0.2H$_2$O); Calcd: C, 51.47; H, 6.11; N, 13.85. Found: C, 51.68; H, 5.97; N, 13.61.

EXAMPLE 2

[(R)-1-((S)-2-Aminopropyl)-7,8-dihydro-1H-[1,4]dioxino[2,3-g]indazol-8-yl]-methanol hydrochloride Step A: {(S)-2-[7-Formyl-6-((S)-1-oxiranylmethoxy)-indazol-1-yl]-1-methyl-ethyl}-carbamic acid benzyl ester.

To a stirred solution of the phenol from Preparation 1 (2.00 g, 5.67 mmol) in anhydrous N,N-dimethylformamide (DMF, 50 mL) was added NaH (60% dispersion in mineral oil, 0.227 g, 5.67 mmol) under nitrogen atmosphere. The mixture was degassed with house vacuum and replaced with nitrogen. After 10 min (2R)-(-)-glycidyl tosylate (1.42 g, 6.24 mmol) was added and the mixture was heated at 75° C. for 2 h. More (2R)-(−)-glycidyl tosylate (0.80 g, 3.51 mmol) and potassium carbonate (0.48 g, 3.47 mmol) were added and heating was continued for an additional 2 h. DMF was evaporated and the residue was mixed with water (50 mL) and 1N HCl to pH 3 and then extracted with ethyl acetate (50 mL×3). The combined extracts were dried over magnesium sulfate, filtered and evaporated to dryness. Chromatography on silica eluting with a gradient of 20% to 80% ethyl acetate/hexane gave the desired product as a solid (1.62 g, 70%). mp 90-92° C., LCMS (+APCI) m/z 410 (M+H), $^1$H NMR (600 MHz, CDCl$_3$) δ 10.67 (s, 1H), 7.95 (s, 1H), 7.89 (d, J=12 Hz, 1H), 7.32-7.26 (m, 5H), 7.22 (d, J=6 Hz, 1H), 6.87 (d, J=6 Hz, 1H), 5.49 (d, J=6 Hz, 1H), 4.97-4.87 (m, 2H), 4.85-4.82 (m, 2H), 4.43 (dd, J=12, 6 Hz, 1H), 4.16 (bd, 2H), 3.41 (s, 1H), 2.96 (1H), 2.78 (m, 1H), 1.19 (d, J=12 Hz, 3H).

Step B: [(S)-2-((R)-8-Hydroxymethyl-7,8-dihydro-[1,4]dioxino[2,3-g]indazol-1-yl)-1-methyl-ethyl]-carbamic acid benzyl ester.

To a stirred solution of the epoxide from Step A (0.86 g, 2.10 mmol) in dichloromethane (100 mL) was added m-chloroperbenzoic acid (70%, 0.62 g, 2.52 mmol) in portions under nitrogen atmosphere. After the addition completed the reaction mixture was stirred overnight. The reaction was quenched by a saturated aqueous solution of sodium thiosulfate (20 mL) and dichloromethane was evaporated. To the aqueous residue was added potassium carbonate (1.0 g) and methanol (200 mL), the resulting mixture was stirred for ½ h and organic solvent was evaporated. The residue was extracted with ethyl acetate (50 mL×3), dried and evaporated to dryness to afford an oil. Chromatography on silica eluting with a gradient of 0% to 10% acetone/dichloromethane gave an oil (0.50 g, 60%). LCMS (+APCI) m/z 397 (M+H), $^1$H NMR (600 MHz, CDCl$_3$) δ 7.82 (s, 1H), 7.33-7.13 (m, 5H), 7.14 (d, J=8.4 Hz, 1H), 6.74 (d, J=8.4 Hz, 1H), 5.04-4.97 (m, 3H), 4.65 (ddd, J=6.6, 13.4, 51.6 Hz, 2H), 4.32 (m, 3H), 4.08 (m, 2H), 3.91 (m, 2H), 1.18(d, J=7.2 Hz, 3H).

Step C: [(R)-1-((S)-2-Aminopropyl)-7,8-dihydro-1H-[1,4]dioxino[2,3-g]indazol-8-yl]-methanol Hydrochloride.

A solution of the alcohol from Step B (0.18 g, 0.45 mmol) and palladium on carbon (10%, 0.014 g) in methanol (50 mL) was stirred under hydrogen atmosphere overnight. The progress of reaction was monitored by TLC. The catalyst was removed by filtration and the filtrate was purified by HPLC eluting with a gradient of 0% to 50% acetonitrile/water/0.1% trifluoroacetic acid. The desired fractions were combined, evaporated and treated a 2N HCl/EtOH (about 2 mL). Evaporation gave a white hygroscopic foamy solid (0.061 g, 45%). mp 112-116° C., LCMS (+APCI) m/z 264 (M+H), $^1$H NMR (600 MHz, CD$_3$OD) δ 7.84 (s, 1H), 7.11 (d, J=8.4, 1H), 6.67 (d, J=9.0 Hz, 1H), 4.70 (dd, J=4.8, 14.4 Hz, 2H), 4.28 (m, 2H), 4.06 (q, J=6.0 Hz, 1H), 3.77 (m, 3H), 1.21 (d, J=6.6 Hz, 3H). Anal. for (C$_{10}$H$_{13}$N$_3$O+HCl+0.2 CF$_3$CO$_2$H+0.2H$_2$O); Calcd: C, 49.35; H, 5.75; N, 12.88. Found: C, 49.48; H, 5.96; N, 12.82.

EXAMPLE 3

(S)-2-(7,8-Dihydro-[1,4]dioxino[2,3-g]indazol-1-yl)-1-methyl-ethylamine hydrochloride Step A: [(S)-2-(7-Bromo-6-hydroxy-indazol-1-yl)-1-methyl-ethyl]-carbamic acid benzyl ester.

To a 0° C. solution of the phenol from Preparation 1 (1.50 g, 4.62 mmol) in anhydrous tetrahydrofuran (100 mL) was added N-bromosuccinimide (0.82 g, 4.62 mmol) with stirring. After 30 min the reaction was completed. The volatile was evaporated and the residue was mixed with a saturated aqueous solution of sodium bicarbonate (100 mL) and extracted with EtOAc (3×100 mL). The combined extracts were dried over magnesium sulfate, filtered and evaporated to afford the desired compound (1.81 g, 97% yield) that was used in the next reaction without further purification. LCMS (+APCI) m/z 404, 406 (M+H).

Step B: [1-((S)-2-Benzyloxycarbonylamino-propyl)-7-bromo-1H-indazol-6-yloxy]-acetic acid ethyl ester.

To a mixture of the compound from Step A (0.90 g, 2.23 mmol), potassium carbonate (0.40 g, 2.90 mmol) in acetone (80 mL) was added ethyl bromoacetate (0.484 g, 0.32 mL, 2.90 mmol) with stirring. The mixture was heated at reflux temperature for 3 h and evaporated to dryness. The residue was mixed with water (100 mL) and extracted with EtOAc (3×60 mL). The combined extracts were dried over magnesium sulfate, filtered and evaporated to dryness. Chromatography on silica eluting with a gradient of 10% to 30% EtOAc/hexane gave a solid (0.92 g, 84%): mp 89-90° C.; LCMS (+APCI) 490, 492 (M+H).

Step C: {(S)-2-[7-Bromo-6-(2-hydroxy-ethoxy)-indazol-1-yl]-1-methyl-ethyl}-carbamic acid benzyl ester.

To a solution of the acetate from Step B (0.90 g, 1.84 mmol) in a mixture of tetrahydrofuran (20 mL) and ethanol (20 mL) was added sodium borohydride (70 mg, 1.84 mmol) and calcium chloride (0.21 g, 1.84 mmol) with stirring. The suspension was stirred at ambient temperature for 1 h and more sodium borohydride (70 mg, 1.84 mmol) was added. The reaction was monitored by TLC until no starting material remained. The volatiles were evaporated and the residue mixed with water and extracted with ethyl acetate (3×50 mL). The combined extracts were dried over magnesium sulfate, filtered and evaporated to dryness. Chromatography on silica eluting with a gradient of 20% to 50% EtOAc/hexane gave a solid (0.67 g, 82%): mp 97-99° C.; LCMS (+APCI) 448, 450 (M+H).

Step D: [(S)-2-(7,8-Dihydro-[1,4]dioxino[2,3-g]indazol-1-yl)-1-methylethyl]-carbamic acid benzyl ester.

To a mixture of the alcohol from Step C (0.36 g, 0.79 mmol) in anhydrous N,N-dimethylformamide (10 mL) was added sodium hydride (60% dispersion in mineral oil, 0.064 mg, 1.59 mmol) and cuprous iodide (0.015 g, 0.79 mmol) under a nitrogen atmosphere with stirring. After 30 min the suspension was heated at 80° C. for 1 h, cooled and mixed with a saturated aqueous solution of sodium bicarbonate (50 mL) and extracted with ethyl acetate (3×50 mL). The combined extracts were dried over magnesium sulfate, filtered and evaporated to dryness. Chromatography on silica eluting with a gradient of 20% to 30% EtOAc/hexane gave an oil (0.056 g, 19%): LCMS (+APCI) 368 (M+H).

Step E: (S)-2-(7,8-Dihydro-[1,4]dioxino[2,3-g]indazol-1-yl)-1-methyl-ethylamine Hydrochloride.

A mixture of the compound from Step D (0.056 g, 0.15 mmol), palladium-on-carbon (10%, 0.005 g) in methanol (10 mL) was stirred under a hydrogen atmosphere overnight. The mixture was filtered and the filtrate was concentrated and purified by HPLC eluting with a gradient of 10% to 50% acetonitrile/water (with 0.1% trifluoroacetic acid). The major fractions were collected, evaporated to dryness and treated with 1 N HCl/ethanol. The salt was evaporated to dryness and dried at 78° C. under high vacuum overnight to afford the desired product as a foamy solid (0.028 g, 69%): LCMS (+APCI) 234 (M+H).

EXAMPLE 4

N-[(S)-1-((S)-2-Amino-propyl)-7,8-dihydro-1H-[1,4]dioxino[2,3-g]indazol-8-ylmethyl]-methanesulfonamide hydrochloride Step A: [(S)-2-((S)-8-Hydroxymethyl-7,8-dihydro-[1,4]dioxino[2,3-g]indazol-1-yl)-1-methylethyl]-carbamic acid tert-butyl ester.

A solution of the compound from Step B of Example 1 (0.95 g, 2.4 mmol), 10% palladium-on-carbon (0.14 g) in methanol (50 mL) was placed under a hydrogen atmosphere overnight. The solution was filtered and the filtrate was evaporated to dryness. To the residue was added dichloromethane (50 mL), di-t-butyl dicarbonate (0.68 g, 3.1 mmol) and trimethylamine (0.36 g, 0.50 mL, 3.6 mmol) with stirring. After 3 h the volatile were evaporated and the residue was purified by chromatography eluting with a gradient of 20% to 40% ethyl acetate/hexane to afford a semi-solid (0.70 g, 80%). LCMS (+APCI) 364 (M+H).

Step B: [(S)-2-((S)-8-Azidomethyl-7,8-dihydro-[1,4]dioxino[2,3-g]indazol-1-yl)-1-methyl-ethyl]-carbamic acid tert-butyl ester.

To a 0° C. stirred solution of the alcohol from Step A (0.69 g, 1.87 mmol) in anhydrous tetrahydrofuran (30 mL) was added triethylamine (0.38 g, 0.52 mL, 3.7 mmol) and methanesulfonic anhydride (0.49 g, 2.81 mmol) under a nitrogen atmosphere. After 1 h the volatiles were evaporated. To the residue was added anhydrous DMSO (40 mL) and sodium azide (2.43 g, 37 mmol). The resulting mixture was heated at 90° C. for 1 h, cooled, mixed with a saturated aqueous solution of sodium bicarbonate (100 mL) and extracted with ethyl acetate (50 mL×3). Chromatography on silica eluting with a gradient of 0% to 25% ethyl acetate/hexane gave an oil (0.65 g, 88%), that solidified on standing. Crystallization from ethyl acetate/hexane gave a crystalline solid (0.48 g, 65%): mp 134-135° C. LCMS (+APCI) 395 (M+H).

Step C: [(S)-2-((S)-8-Aminomethyl-7,8-dihydro-[1,4]dioxino[2,3-g]indazol-1-yl)-1-methyl-ethyl]-carbamic acid tert-butyl ester.

A solution of the azide from Step B (0.48 g, 1.24 mmol), 10% palladium-on-carbon (0.05 g) in methanol (50 mL) was stirred under a hydrogen atmosphere overnight. The mixture was filtered and evaporated to give an oil (0.48 g, 100%). LCMS (+APCI) 363 (M+H).

Step D: {(S)-2-[(S)-8-(Methanesulfonylamino-methyl)-7,8-dihydro-[1,4]dioxino[2,3-g]indazol-1-yl]-1-methyl-ethyl}-carbamic acid tert-butyl ester.

To a 0° C. stirred solution of the amine from Step C (0.12 g, 0.33 mmol) in anhydrous dichloromethane (20 mL) was added trimethylamine (0.066 g, 0.65 mmol) and methanesulfonic anhydride (0.086 mg, 0.050 mmol) under nitrogen. After the addition completed, the mixture was warmed to ambient temperature, stirred for 1 h and evaporated to dryness. Chromatography on silica eluting with a gradient of 10% to 60% ethyl acetate/hexane gave an oil (0.090 g, 63%). LCMS(+APCI) 441(M+H).

Step E: N-[(S)-1-((S)-2-Amino-propyl)-7,8-dihydro-1H-[1,4]dioxino[2,3-g]indazol-1ylmethyl]-methanesulfonamide Hydrochloride.

A solution of the compound from Step D (0.090 g, 0.20 mmol) in trifluoroacetic acid (3 mL) was stirred overnight under a nitrogen atmosphere. The mixture was evaporated to dryness, treated with 1 N HCl/EtOH (1 mL) and evaporated to dryness. Crystallization from MeOH/$CH_2Cl_2$ gave a solid (0.039 g, 52%): LCMS (+APCI) 341 (M+H); mp 235-236° C. Calcd. for $C_{14}H_{20}N_4O_4S$+HCl: C, 44.62; H, 5.62; N, 14.87. Found: C, 44.92; H, 5.65; N, 14.82.

EXAMPLE 5

Ethanesulfonic acid [(S)-1-((S)-2-amino-propyl)-7,8-dihydro-1H-[1,4]dioxino[2,3-g]indazol-8-ylmethyl]-amide hydrochloride Using the same procedure as Example 4 and ethanesulfonic anhydride, the title compound was prepared as a solid: mp 243-244° C.; LCMS (+APCI) 355 (M+H). Calcd. for $C_{15}H_{22}N_4O_4S$+HCl: C, 46.09; H, 5.93; N, 14.33. Found: C, 46.09; H, 5.93; N, 14.26.

EXAMPLE 6

N-[(S)-1-((S)-2-Amino-propyl)-7,8-dihydro-1H-[1,4]dioxino[2,3-g]indazol-8-ylmethyl]-isobutyramide hydrochloride Using the same procedure as Example 4 and isobutyryl chloride, the title compound was prepared as a semi-solid; LCMS (+APCI) 333 (M+H). Calcd. for $C_{17}H_{24}N_4O_4$+$H_2O$+0.1 EtOAc+HCl: C, 52.82; H, 7.08; N, 14.16. Found: C, 52.51; H, 6.91; N, 13.77.

EXAMPLE 7

[(S)-1-((S)-2-Amino-propyl)-7,8-dihydro-1H-[1,4]dioxino[2,3-g]indazol-8-ylmethyl]-carbamic acid methyl ester hydrochloride Using the same procedure as Example 4 and methyl chloroformate, the title compound was prepared as a solid: mp 265-266° C.; LCMS (+APCI) 321 (M+H). Calcd. for $C_{15}H_{20}N_4O_4$+HCl: C, 50.49; H, 5.93; N, 15.70. Found: C, 50.58; H, 6.00; N, 15.47.

EXAMPLE 8

(S)-2-((S)-8-Aminomethyl-7,8-dihydro-[1,4]dioxino[2,3-g]indazol-1-yl)-1-methyl-ethylamine hydrochloride Step A: [(S)-2-((S)-8-Azidomethyl-7,8-dihydro-[1,4]dioxino[2,3-g]indazol-1-yl)-1-methyl-ethyl]-carbamic acid benzyl ester.

To a ° C. stirred solution of the alcohol from Step B of Example 1 (0.43 g, 1.08 mmol) in anhydrous tetrahydrofuran (30 mL) was added triethylamine (0.88 g, 8.6 mmol) and methanesulfonic anhydride (0.76 g, 4.4 mmol) under nitrogen atmosphere. After 1 h the volatiles were evaporated. To the residue was added anhydrous DMSO (30 mL) and sodium azide (0.7 g, 11 mmol). The resulting mixture was heated at 85° C. for 3 h, 95° C. for 1 h, cooled, mixed with a saturated aqueous solution of sodium bicarbonate (100 mL) and extracted with ethyl acetate (50 mL×3). Chromatography on silica eluting with a gradient of 15% to 60% ethyl acetate/hexane gave an oil (0.29 g, 63%): LCMS (+APCI) 423 (M+H).

Step B: (S)-2-((S)-8-Aminomethyl-7,8-dihydro-[1,4]dioxino[2,3-g]indazol-1-yl)-1-methyl-ethylamine hydrochloride.

A mixture of the compound from Step A (0.13 g, 0.31 mmol), palladium-on-carbon (10%, 0.05 g) in methanol (10 mL) was stirred under a hydrogen atmosphere overnight. The mixture was filtered and the filtrate was concentrated and purified by HPLC eluting with a gradient of 0% to 50% acetonitrile/water (with 0.1% trifluoroacetic acid). The major fractions were collected, evaporated to dryness and treated with 1 N HCl/ethanol. The salt was evaporated to dryness and dried at 78° C. under high vacuum overnight to afford the desired product as a foamy solid (0.06 g, 65%): LCMS (+APCI) 263 (M+H).

EXAMPLE 9

[(R)-1-((S)-2-Amino-propyl)-7,8-dihydro-1H-[1,4]dioxino[2,3-g]indazol-8-ylmethyl]-carbamic acid methyl ester hydrochloride Using the procedure of Example 7 and the compound from Step B of Example 2, the title compound was prepared as an off-white solid: LCMS (+APCI) 321 (M+H). Calcd. for $C_{15}H_{20}N_4O_4$+HCl+0.2$H_2O$: C, 49.99; H, 5.98; N, 15.55. Found: C, 49.89; H, 5.95; N, 15.40.

The following methods can be used to characterize the compounds of the present invention.

Method 1: 5-$HT_2$ Receptor Binding Assay

In order to determine the relative affinities of serotonergic compounds at the 5-$HT_2$ receptors, their ability to compete for the binding of the agonist radioligand [$^{125}$I]DOI to brain 5-$HT_2$ receptors is determined as described below with minor modification of the literature procedure [Neuropharmacology, 26, 1803 (1987)]. Aliquots of post mortem rat or human cerebral cortex homogenates (400 μl) dispersed in 50 mM Tris HCl buffer (pH 7.4) are incubated with [$^{125}$I]DOI (80 pM final) in the absence or presence of methiothepin (10 μM final) to define total and non-specific binding, respectively, in a total volume of 0.5 ml. The assay mixture is incubated for 1 hour at 23° C. in polypropylene tubes and the assays terminated by rapid vacuum filtration over Whatman GF/B glass fiber filters previously soaked in 0.3% polyethyleneimine using ice-cold buffer. Test compounds (at different concentrations) are substituted for methiothepin. Filter-bound radioactivity is determined by scintillation spectrometry on a beta counter. The data are analyzed using a non-linear, iterative curve-fitting computer program [Trends Pharmacol. Sci., 16, 413 (1995)] to determine the compound affinity parameter. The concentration of the compound needed to inhibit the [$^{125}$I]DOI binding by 50% of the maximum is termed the $IC_{50}$ or $K_i$ value.

Method 2: 5-$HT_2$ Functional Assay: [$Ca^{2+}$]$_i$ Mobilization

The receptor-mediated mobilization on intracellular calcium ([$Ca^{2+}$]$_i$) was studied using the Fluorescence Imaging Plate Reader (FLIPR) instrument. Rat vascular smooth muscle cells, A7r5, were grown in a normal media of DMEM/10% FBS and 10 μg/mL gentamycin. Confluent cell monolayers were trypsinized, pelleted, and re-suspended in normal media. Cells were seeded in a 50 SL volume at a density of 20,000 cells/well in a black wall, 96-well tissue culture plate and grown for 2 days.

On the day of the experiment, one vial of FLIPR Calcium Assay Kit dye was re-suspended in 50 mL of a FLIPR buffer consisting of Hank's Balanced Salt Solution (HBSS), 20 mM HEPES, and 2.5 mM probenecid, pH 7.4. Cells were loaded with the calcium-sensitive dye by addition of an equal volume (50 μL) to each well of the 96-well plate and incubated with dye for 1 h at 23° C.

Typically, test compounds were stored at 25 μM in 50% DMSO/50% Ethanol solvent. Compounds were diluted 1:50 in 20% DMSO/20% Ethanol. For "hit" screening, compounds were further diluted 1:10 in FLIPR buffer and tested at a final concentration of 10 μM. For dose-response experiments, compounds were diluted 1:50 in FLIPR buffer and serially diluted 1:10 to give a 5- or 8-point dose-response curve.

The compound plate and cell plate were placed in the FLIPR instrument. At the beginning of an experimental run, a signal test was performed to check the basal fluorescence signal from the dye-loaded cells and the uniformity of the signal across the plate. The basal fluorescence was adjusted between 8000-12000 counts by modifying the exposure time, the camera F-stop, or the laser power. Instrument settings for a typical assay were the following: laser power 0.3-0.6 W, camera F-stop F/2, and exposure time 0.4 sec. An aliquot (25 μL) of the test compound was added to the existing 100 μL dye-loaded cells at a dispensing speed of 50 μL/sec. Fluorescence data were collected in real-time at 1.0 sec intervals for the first 60 secs and at 6.0 sec intervals for an additional 120 secs. Responses were measured as peak fluorescence intensity minus basal and where appropriate were expressed as a percentage of a maximum 5-HT-induced response. When the compounds were tested as antagonists against 10 μM 5-HT, they were incubated with the cells for 15 minutes prior to the addition of 5-HT.

The above procedures were used to generate the data shown in Table 3.

TABLE 3

5-HT2 Receptor Binding and Functional Data.

| Example | IC50, nM | EC50, nM | Efficacy (Emax, %) |
| --- | --- | --- | --- |
| 1 | 0.96 | 31 | 39 |
| 2 | 1.2 | 53 | 77 |
| 3 | 0.57 | 27 | 92 |
| 4 | 3.1 | 78 | 81 |
| 5 | 7.0 | 67 | 82 |
| 6 | 4.2 | 125 | 59 |
| 7 | 1.9 | 92 | 66 |
| 8 | 11 | 232 | 54 |
| 9 | 3.1 | 106 | 44 |

Method 3: Acute IOP Response in Lasered (Hypertensive) Eyes of Conscious Cynomolgus Monkeys Intraocular pressure (IOP) can be determined with an Alcon Pneumatonometer after light corneal anesthesia with 0.1% proparacaine. Eyes are washed with saline after each measurement. After a baseline IOP measurement, test compound is instilled in one 30 μL aliquot to the right eyes only of nine cynomolgus monkeys. Vehicle is instilled in the right eyes of six additional animals. Subsequent IOP measurements are taken at 1, 3, and 6 hours.

The above method was used to determine the IOP lowering efficacy of the compound of Example 1 (dosed at a concentration of 300 μg). The results are shown in Table 4.

TABLE 4

| | IOP Efficacy. | | | |
|---|---|---|---|---|
| | Example 1 | | Vehicle Control | |
| Time (hrs.) | IOP Change mmHg | IOP % change | IOP Change mmHg | IOP % Change |
| 1 | −2.2 | −4.3 | 0.7 | 1.8 |
| 3 | −6.8 | −15.8 | −0.8 | −2.1 |
| 6 | −9.6 | −23.6 | −2.7 | −6.7 |

The compound of formula (I) and its salts and esters (collectively, compounds of formula (I)) can be incorporated into various types of ophthalmic formulations for delivery to the eye (e.g., topically, intracamerally, or via an implant). The compounds of formula (I) are preferably incorporated into topical ophthalmic formulations for delivery to the eye. The compounds may be combined with ophthalmologically acceptable preservatives, surfactants, viscosity enhancers, penetration enhancers, buffers, sodium chloride, and water to form an aqueous, sterile ophthalmic suspension or solution. Ophthalmic solution formulations may be prepared by dissolving a compound of formula (I) in a physiologically acceptable isotonic aqueous buffer. Further, the ophthalmic solution may include an ophthalmologically acceptable surfactant to assist in dissolving the compound of formula (I). Furthermore, the ophthalmic solution may contain an agent to increase viscosity, such as, hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the compound of formula (I) in a hydrophilic base prepared from the combination of, for example, carbopol-974, or the like, according to the published formulations for analogous ophthalmic preparations; preservatives and tonicity agents can be incorporated.

The compounds of formula (I) are preferably formulated as topical ophthalmic suspensions or solutions, with a pH of about 4 to 8. The compounds of formula (I) will normally be contained in these formulations in an amount 0.01 to 5% (w/v), but preferably in an amount of 0.1 to 2% (w/v). Thus, for topical presentation 1 to 2 drops of these formulations would be delivered to the surface of the eye 1 to 4 times per day according to the discretion of a skilled clinician.

The compounds of formula (I) can also be used in combination with other agents for treating glaucoma, such as, but not limited to, β-blockers (e.g., timolol, betaxolol, levobetaxolol, carteolol, levobunolol, propranolol), carbonic anhydrase inhibitors (e.g., brinzolamide and dorzolamide), $\alpha_1$ antagonists (e.g. nipradolol), $\alpha_2$ agonists (e.g., iopidine and brimonidine), miotics (e.g., pilocarpine and epinephrine), prostaglandin analogs (e.g., latanoprost, travaprost, unoprostone, and compounds set forth in U.S. Pat. Nos. 5,889,052; 5,296,504; 5,422,368; and 5,151,444, "hypotensive lipids" (e.g., lumigan and compounds set forth in U.S. Pat. No. 5,352,708), and neuroprotectants (e.g., compounds from U.S. Pat. No. 4,690,931, particularly eliprodil and R-eliprodil, as set forth in a pending application U.S. Ser. No. 06/203350, and appropriate compounds from WO94/13275, including memantine.

The following topical ophthalmic formulations are useful according to the present invention administered 1-4 times per day according to the discretion of a skilled clinician.

EXAMPLE 10

| Ingredients | Amount (wt %) |
|---|---|
| Compound of Formula I | 0.1-2% |
| Hydroxypropyl methylcellulose | 0.5% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydroxide acid | For adjusting pH to 6.8-7.4 |
| Purified water | q.s. to 100% |

EXAMPLE 11

| Ingredients | Amount (wt %) |
|---|---|
| Compound of Formula I | 0.1-2% |
| Methyl cellulose | 4.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 6.8-7.4 |
| Purified water | q.s. to 100% |

EXAMPLE 12

| Ingredients | Amount (wt %) |
|---|---|
| Compound of Formula I | 0.1-2% |
| Guar gum | 0.4-6.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 6.8-7.4 |
| Purified water | q.s. to 100% |

EXAMPLE 13

| Ingredients | Amount (wt %) |
|---|---|
| Compound of Formula I | 0.1-2% |
| White petrolatum and mineral oil and lanolin | Ointment consistency |
| Dibasic sodium phosphate (anhydrous) | 0.2% |
| Sodium chloride | 0.5% |
| Disodium EDTA (Edetate disodium) | 0.01% |

| Ingredients | Amount (wt %) |
|---|---|
| Polysorbate 80 | 0.05% |
| Benzalkonium chloride | 0.01% |
| Sodium hydroxide/Hydrochloric acid | For adjusting pH to 6.8-7.4 |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and structurally related may be substituted for the agents described herein to achieve similar results. All such substitutions and modifications apparent to those skilled in the art are deemed to be within the spirit, scope and concept of the invention as defined by the appended claims.

REFERENCES

All references cited herein, to the extent that they provide exemplary procedural or other details supplementary to those set forth herein, are specifically incorporated herein by reference.

What is claimed is:

1. A compound represented by Formula 1:

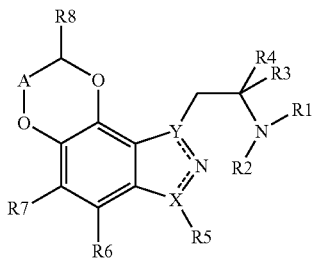

(I)

wherein $R^1$ and $R^2$ are independently chosen from hydrogen or an alkyl group;
$R^3$ and $R^4$ are independently hydrogen or an alkyl group or;
$R^3$ and $R^4$ and the carbon atom to which they are attached form a cycloalkyl ring, or;
$R^2$ and $R^3$ together form a saturated $(CH_2)_m$ heterocycle;
$R^5$ is hydrogen, halogen, or a substituted or unsubstituted alkyl group;
$R^6$ and $R^7$ are independently hydrogen, halogen, cyano, an alkylthio or a substituted or unsubstituted alkyl group;
$R^8$ and $R^9$ are independently hydrogen, an alkyl group, an alkoxy, =O, $NR^{10}R^{11}$, $OC(=O)NR^1R^2$, $OC(=O)C_{1-4}$ alkyl, an alkylthiol, or an alkyl substituted with halogen, $NR^{10}R^{11}$, $OR^{12}$, $CO_2R^{13}$, $CONR^{14}R^{15}$, $SO_2R^{12}$, $NSO_2R^{12}$, or $SO_2NR^{10}R^{11}$;
$R^{10}$ and $R^{11}$ are independently hydrogen, a substituted or unsubstituted alkyl group, $C(=O)C_{1-4}$ alkyl, $C(=O)OC_{1-4}$ alkyl, $C(=O)NR^1R^2$ or $R^{10}$ and $R^{11}$ together complete a saturated 5 or 6-membered heterocyclic ring, which can include an additional heteroatom selected from N, O, or S when a 6-membered ring;
$R^{12}$ is hydrogen, $C_{1-6}$ alkyl, $C(=O)C_{1-6}$alkyl, $C(=O)OC_{1-6}$ alkyl, $C(=O)$ $N(R^{13})C_{1-6}$alkyl or $C(=O)C_{1-6}$ alkyl substituted with hydroxyl, $C_{1-4}$alkoxide, or halide;
$R^{13}$ is hydrogen, $C_{1-6}$alkyl, $C_{1-6}$alkyl substituted by hydroxyl, $C_{1-4}$alkoxy, or halide;
$R^{14}$ and $R^{15}$ are independently chosen from hydrogen, hydroxyl, $C_{1-4}$alkoxy, $C_{1-6}$alkyl, $C_{2-6}$alkyl substituted by hydroxyl, $C_{1-4}$alkoxy, halide, or $R^{14}$ and $R^{15}$ can be combined to form a saturated heterocyclic ring selected from pyrrolidine, piperidine, piperazine, or morpholine;
m=2-4;
A=$CHR^9$ or no atom;
X and Y are either N or C, wherein X and Y are different from each other; and
the dashed bonds denotes a suitably appointed single and double bond.

2. The compound of claim 1, wherein said $R^2$ and $R^3$ form a saturated $(CH_2)_m$ heterocycle.

3. The compound of claim 1, wherein said $R^3$ and $R^4$ form a cyclopropyl ring.

4. The compound of claim 1, wherein $R^1$ and $R^2$ are independently chosen from hydrogen or $C_{1-4}$ alkyl;
$R^3$ and $R^4$ are independently chosen from hydrogen or $C_{1-4}$ alkyl or $R^2$ and $R^3$ together can be $(CH_2)_m$ to form a saturated heterocycle;
$R^5$ is chosen from hydrogen, halogen, or $C_{1-6}$ alkyl;
$R^6$ and $R^7$ are independently chosen from hydrogen, halogen, cyano, $C_{1-4}$ alkylthio, $C_{1-4}$ alkyl, or $C_{1-4}$ alkyl substituted by halogen;
$R^8$ and $R^9$ are independently chosen from hydrogen, $C_{1-6}$ alkyl, $C_{1-6}$alkoxy, =O, $NR^{10}R^{11}$, $OC(=O)NR^1R^2$, $OC(=O)C_{1-4}$alkyl, a $C_{1-6}$ alkyl substituted with halogen, or $NR^{10}R^{11}$, $OR^{11}$, $CO_2R^{11}$, $CONR^{10}R^{11}$, $SO_2R^{11}$, $NSO_2R^{11}$, $SO_2NR^{10}R^{11}$;
$R^{10}$ and $R^{11}$ are independently chosen from hydrogen, $C_{1-4}$ alkyl, $C(=O)C_{1-4}$ alkyl, $C(=O)OC_{1-4}$ alkyl, $C(=O)NR^1R^2$, or $C_{1-4}$ alkyl substituted with halogen, hydroxyl, $NR^1R^2$ or $R^{10}$ and $R^{11}$ together can complete a saturated 5 or 6-membered heterocyclic ring, which can include an additional heteroatom selected from N, O, or S;
m=2-4;
A=$CHR^9$ or no atom;
X and Y are either N or C, wherein X and Y are different from each other; and
the dashed bonds denotes a suitably appointed single and double bond.

5. The compound of claim 1, wherein $R^1$ and $R^2$ are independently chosen from hydrogen or $C_{1-4}$ alkyl;
$R^3$ is $C_{1-2}$ alkyl or $R^2$ and $R^3$ together can be $(CH_2)_3$ to form a pyrrolidine;
$R^4$ is hydrogen;
$R^5$ is chosen from hydrogen, halogen, or $C_{1-4}$ alkyl;
$R^6$ and $R^7$ are independently chosen from hydrogen, halogen, $C_{1-4}$ alkyl;
$R^8$ and $R^9$ are independently chosen from hydrogen, $C_{1-4}$ alkyl, a $C_{1-4}$ alkyl substituted with halogen, or $NR^{10}R^{11}$, $OR^{11}$, $CO_2R^{11}$, $CONR^{10}R^{11}$, $SO_2R^{11}$, $NSO_2R^{11}$;
$R^{10}$ and $R^{11}$ are independently chosen from hydrogen, $C_{1-4}$ alkyl, $C(=O)C_{1-4}$ alkyl, $C(=O)OC_{1-4}$ alkyl, $C(=O)NR^1R^2$, or $C_{1-4}$ alkyl substituted with halogen, hydroxyl, $NR^1R^2$ or $R^{10}$ and $R^{11}$ together can complete a saturated 5 or 6-membered heterocyclic ring, which can include an additional heteroatom selected from N, O, or S;
X and Y are either N or C, wherein X and Y are different from each other; and the dashed bonds denotes a suitably appointed single and double bond.

6. The compound of claim 1, wherein said compound is selected from the group consisting of:

2-(7,8-Dihydro-[1,4]dioxino[2,3-g]indazol-1-yl)-1-methyl-ethylamine;

(S)-2-(7,8-Dihydro-[1,4]dioxino[2,3-g]indazol-1-yl)-1-methyl-ethylamine;

(R)-2-(7,8-Dihydro-[1,4]dioxino[2,3-g]indazol-1-yl)-1-methyl-ethylamine;

[1-(2-Amino-propyl)-7,8-dihydro-1H-[1,4]dioxino[2,3-g]indazol-8-yl]-methanol;

[1-((S)-2-Amino-propyl)-7,8-dihydro-1H-[1,4]dioxino[2,3-g]indazol-8-yl]-methanol;

[(R)-1-((S)-2-Amino-propyl)-7,8-dihydro-1H-[1,4]dioxino[2,3-g]indazol-8-yl]-methanol;

[(S)-1-((S)-2-Amino-propyl)-7,8-dihydro-1H-[1,4]dioxino[2,3-g]indazol-8-yl]-methanol;

N-[1-((S)-2-Amino-propyl)-7,8-dihydro-1H-[1,4]dioxino[2,3-g]indazol-8-ylmethyl]-methanesulfonamide;

N-[(S)-1-((S)-2-Amino-propyl)-7,8-dihydro-1H-[1,4]dioxino[2,3-g]indazol-8-ylmethyl]-methanesulfonamide;

Ethanesulfonic acid [1-((S)-2-amino-propyl)-7,8-dihydro-1H-[1,4]dioxino[2,3-g]indazol-8-ylmethyl]-amide;

Ethanesulfonic acid [1-((S)-2-amino-propyl)-7,8-dihydro-1H-[1,4]dioxino[2,3-g]indazol-8-ylmethyl]-amide;

[1-((S)-2-Amino-propyl)-7,8-dihydro-1H-[1,4]dioxino[2,3-g]indazol-8-ylmethyl]-carbamic acid methyl ester;

[(S)-1-((S)-2-Amino-propyl)-7,8-dihydro-1H-[1,4]dioxino[2,3-g]indazol-8-ylmethyl]-carbamic acid methyl ester;

2-((S)-8-Aminomethyl-7,8-dihydro-[1,4]dioxino[2,3-g]indazol-1-yl)-1-methyl-ethylamine;

(S)-2-((S)-8-Aminomethyl-7,8-dihydro-[1,4]dioxino[2,3-g]indazol-1-yl)-1-methyl-ethylamine;

N-({1-[(S)-2-aminopropyl]-7,8-dihydro-1H-[1,4]dioxino[2,3-g]indazol-8-yl}methyl)acetamide;

N-({(S)-1-[(S)-2-aminopropyl]-7,8-dihydro-1H-[1,4]dioxino[2,3-g]indazol-8-yl}methyl)acetamide;

1-(1H-[1,3]dioxolo[4,5-g]indazol-1-yl))-1-methyl-ethylamine; and (S)-1-(1H-[1,3]dioxolo[4,5-g]indazol-1-yl))-1-methyl-ethyl amine.

7. The compound of claim 1, wherein said X is N.

8. The compound of claim 2, wherein said X is C.

9. A method of controlling of normal or elevated intraocular pressure in an eye of a patient comprising administering to the patient a composition comprising a pharmaceutically effective amount of a compound represented by Formula 1:

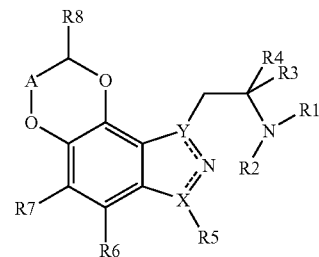

(I)

wherein $R^1$ and $R^2$ are independently chosen from hydrogen or an alkyl group;

$R^3$ and $R^4$ are independently hydrogen or an alkyl group or;

$R^3$ and $R^4$ and the carbon atom to which they are attached form a cycloalkyl ring, or;

$R^2$ and $R^3$ together form a saturated $(CH_2)_m$ heterocycle;

$R^5$ is hydrogen, halogen, or a substituted or unsubstituted alkyl group;

$R^6$ and $R^7$ are independently hydrogen, halogen, cyano, an alkylthio or a substituted or unsubstituted alkyl group;

$R^8$ and $R^9$ are independently hydrogen, an alkyl group, an alkoxy, =O, $NR^{10}R^{11}$, $OC(=O)NR^1R^2$, $OC(=O)C_{1-4}$ alkyl, an alkylthiol, or an alkyl substituted with halogen, $NR^{10}R^{11}$, $OR^{12}$, $CO_2R^{13}$, $CONR^{14}R^{15}$, $SO_2R^{12}$, $NSO_2R^{12}$, or $SO_2NR^{10}R^{11}$;

$R^{10}$ and $R^{11}$ are independently hydrogen, a substituted or unsubstituted alkyl group, $C(=O)C_{1-4}$ alkyl, $C(=O)OC_{1-4}$ alkyl, $C(=O)NR^1R^2$ or $R^{10}$ and $R^{11}$ together complete a saturated 5 or 6-membered heterocyclic ring, which can include an additional heteroatom selected from N, O, or S when a 6-membered ring;

$R^{12}$ is hydrogen, $C_{1-6}$ alkyl, $C(=O)C_{1-6}$alkyl, $C(=O)OC_{1-6}$alkyl, $C(=O)$ $N(R^{13})C_{1-6}$alkyl or $C(=O)C_{1-6}$alkyl substituted with hydroxyl, $C_{1-4}$alkoxide, or halide;

$R^{13}$ is hydrogen, $C_{1-6}$alkyl, $C_{1-6}$alkyl substituted by hydroxyl, $C_{1-4}$alkoxy, or halide;

$R^{14}$ and $R^{15}$ are independently chosen from hydrogen, hydroxyl, $C_{1-4}$alkoxy, $C_{1-6}$alkyl, $C_{2-6}$alkyl substituted by hydroxyl, $C_{1-4}$alkoxy, halide, or $R^{14}$ and $R^{15}$ can be combined to form a saturated heterocyclic ring selected from pyrrolidine, piperidine, piperazine, or morpholine;

m=2-4;

A=$CHR^9$ or no atom;

X and Y are either N or C, wherein X and Y are different from each other; and the dashed bonds denotes a suitably appointed single and double bond.

10. The method of claim 9 wherein the composition is topically administered to the eye.

* * * * *